US00PP09770P

United States Patent [19]

Lopez

[11] Patent Number: Plant 9,770

[45] Date of Patent: Dec. 31, 1996

[54] STRAWBERRY PLANT NAMED 'ARENA'

[75] Inventor: Jose M. A. Lopez, Tudela, Spain

[73] Assignee: Plantas de Navarra, S.A., Navarra, Spain

[21] Appl. No.: 513,006

[22] Filed: Aug. 9, 1995

[51] Int. Cl.[6] ..... A01H 5/00

[52] U.S. Cl. ..... Plt./48

[58] Field of Search ..... Plt./48, 49

[56] References Cited

U.S. PATENT DOCUMENTS

P.P. 5,262 7/1984 Voth et al. ..... Plt./48

*Primary Examiner*—James R. Feyrer

*Attorney, Agent, or Firm*—Christie, Parker & Hale, LLP

[57] ABSTRACT

A strawberry plant producing conical to almost cylindrically shaped fruit and having inflorescence extending beneath the foliage.

9 Drawing Sheets

BACKGROUND OF THE INVENTION

The new variety of strawberry was created in a breeding program by my crossing two parents from among a group of seedlings which were obtained from a free pollination of 32 different varieties and seedlings; in particular, by crossing as seed parent a variety designated 85-20 and as a pollen parent a variety designated 86-175. Both parental varieties are proprietary and have not been commercialized.

The resulting seedling of the new variety was grown and asexually propagated by runners in Soria, Spain, 3°W., 41°N., 3000 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Arena', among the charcteristics which distinguish the new variety from other varieties of which I am aware are a combination of traits which include inflorescence that appears beneath the foliage and abundant production of red colored and conical to almost cylindrically shaped fruit.

COMPARISON TO CLOSEST VARIETY

The new variety is closest to the variety 'Chandler' (U.S. Plant Pat. No. 5262), but is distinguished therefrom by the following characteristics possessed by 'Arena' which are different than, or not possessed by, 'Chandler'.

1. Chandler exhibits more plant vigor than 'Arena'.

2. 'Arena' has a darker green leaf color than 'Chandler'.

3. Leaf surface undulation of 'Chandler' is less than in 'Arena'. The differences in the leaves of 'Chandler' and the new variety are shown in FIG. 8. These differences are maintained during the growing season.

4. Terminal leaflet of 'Arena' is longer than broad whereas in 'Chandler' the terminal leaflet is as long as broad.

5. Stipule coloration is absent or very weak in 'Chandler' and is well noted in 'Arena'. The stipules of 'Arena' exhibit a reddish coloration, as shown in FIG. 9, and are more open than the stipules of 'Chander' which do not display the reddish color to the same extent and are more closed. This difference is maintained through the growing period.

6. Inflorescence position of 'Chandler' is level with foliage; in 'Arena' the inflorescence is beneath.

7. Calyx relative to corolla is same size in 'Chandler', whereas in 'Arena' it is larger.

8. 'Chandler' fruit shape is long-wedged. Fruit shape of 'Arena' is consical, almost cylindrical.

9. Fruit surface of 'Chandler' is a bit more irregular than in 'Arena'.

10. 'Chandler' fruit color is purple but red in 'Arena'.

11. 'Chandler' calyx is larger than the fruit and in 'Arena' it is the same size.

12. 'Chandler' flesh color is even but is slightly uneven in 'Arena'.

BRIEF DESCRIPTION OF ILLUSTRATION

The accompanying photographs show typical specimens of the new variety, designated s 90-32-013 in the illustrations, including fruit, foliage and flower, in color as nearly true as it is reasonably possible to make in color illustrations of this character.

Figure 1:
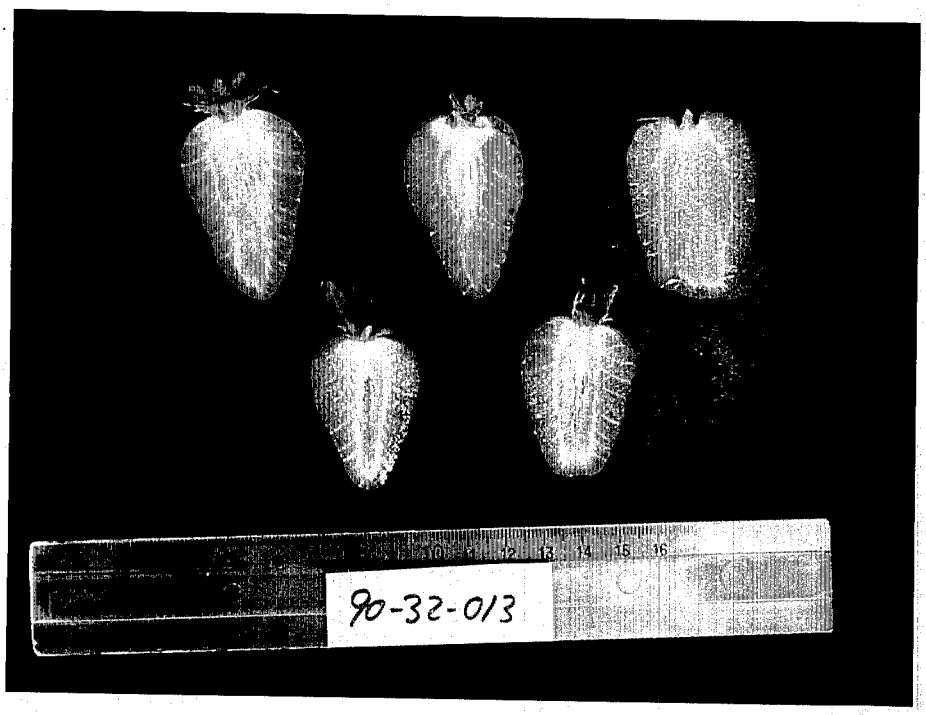
FIG. 1 shows typical fruit in cross section illustrating the typical flesh and fleshcoloration, conspicuous core and core cavity and conical almost cylindrical shape.
Figure 2:
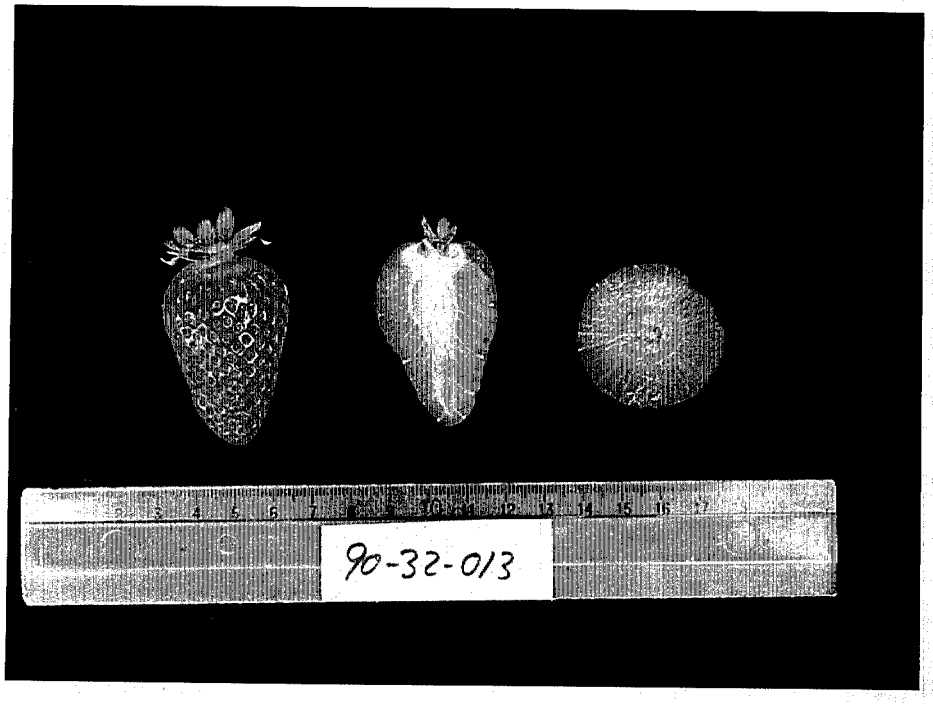
FIG. 2 shows whole and sliced, detached fruit.
Figure 3:
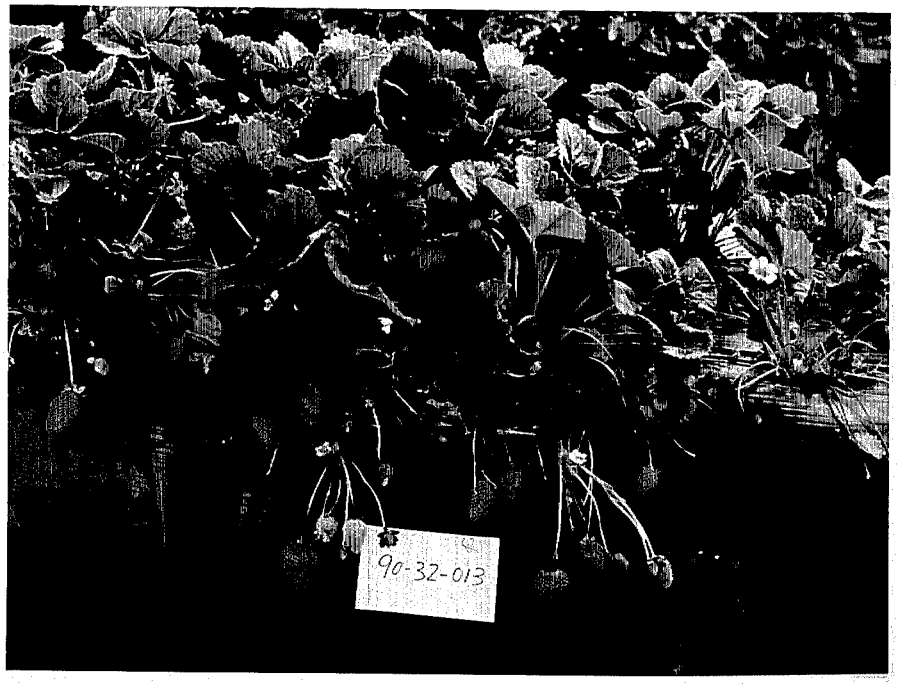
FIGS. 3 and 4 show the fruit against a background of the top surface of the foliage.
Figure 4:
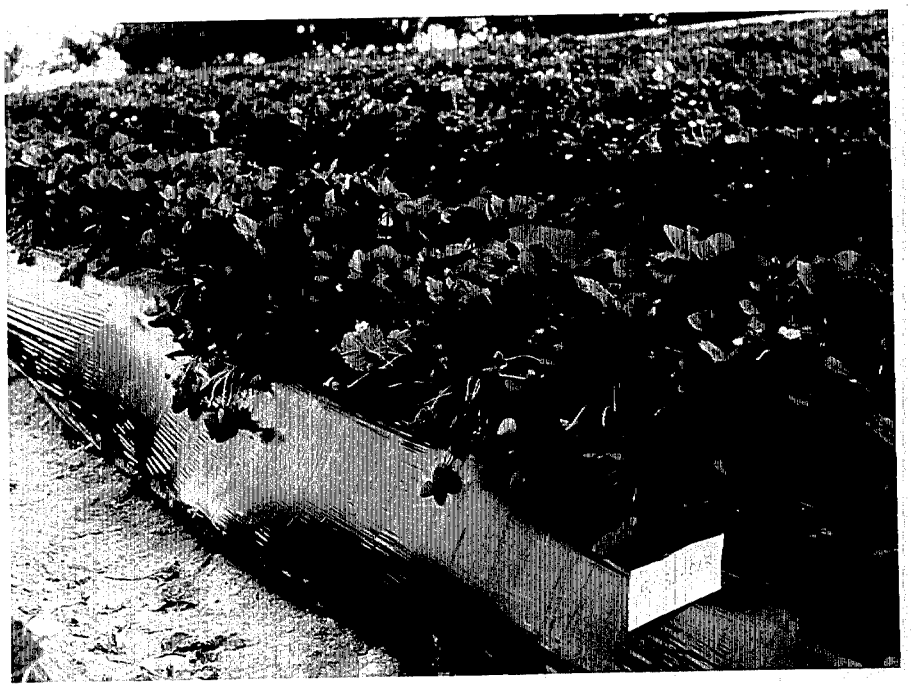
Figure 5:
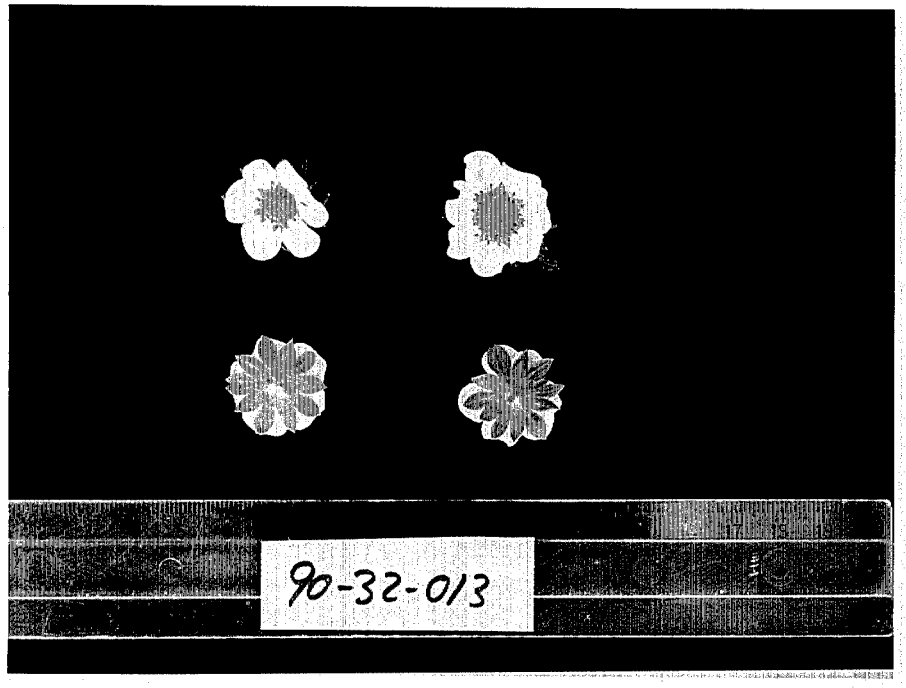
FIG. 5 shows the flower and reproductive organs of the new variety.
Figure 6:
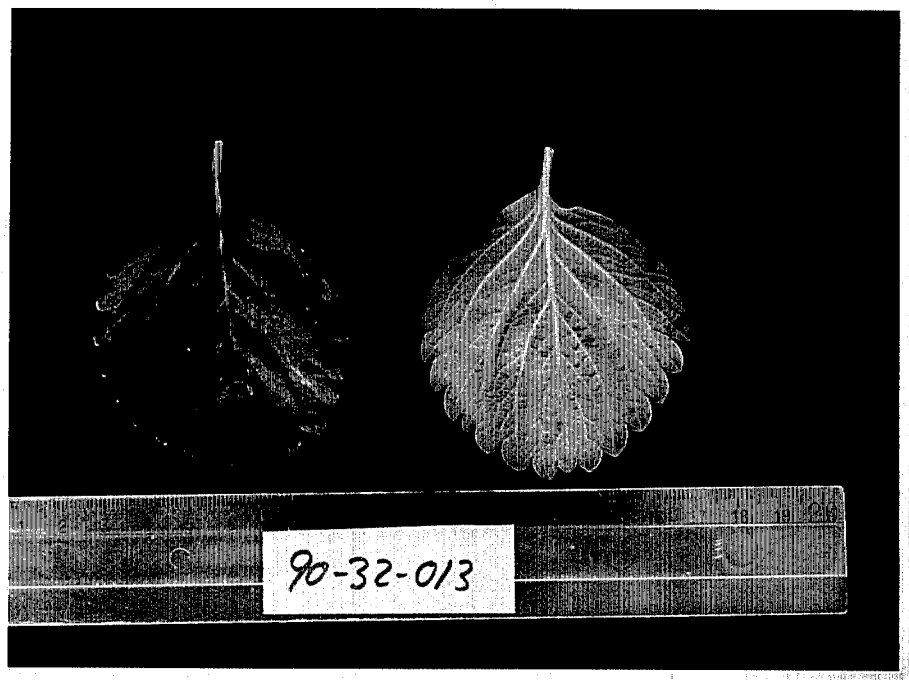
FIG. 6 shows the top and undersurface of a typical foliole of the new variety.
Figure 7:
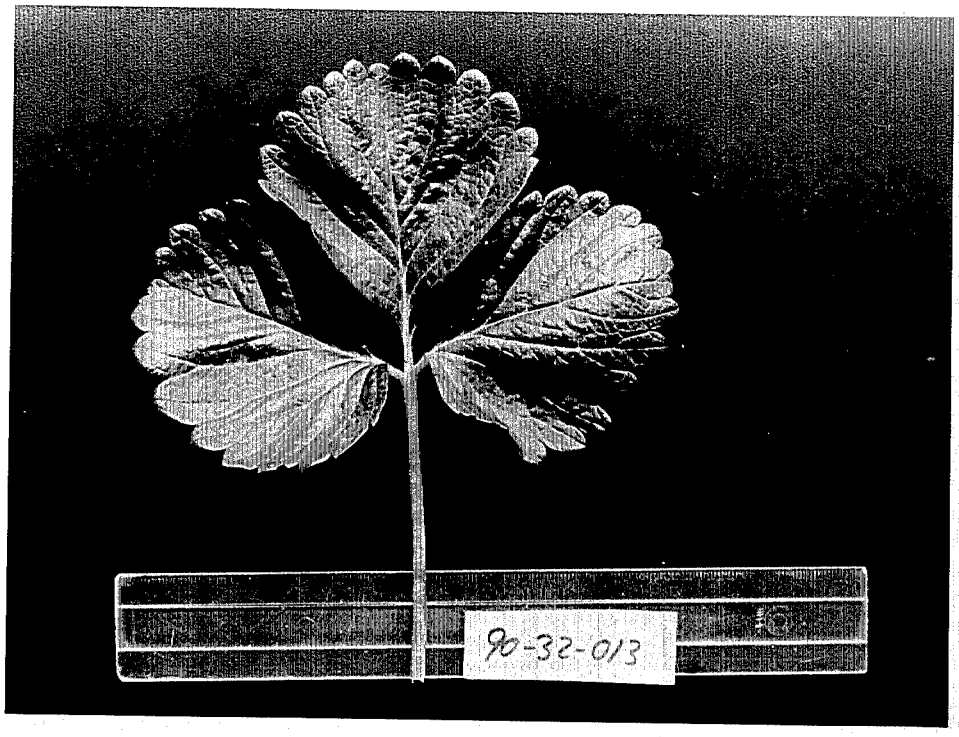
FIG. 7 shows a typical leave of the new variety.
Figure 8:
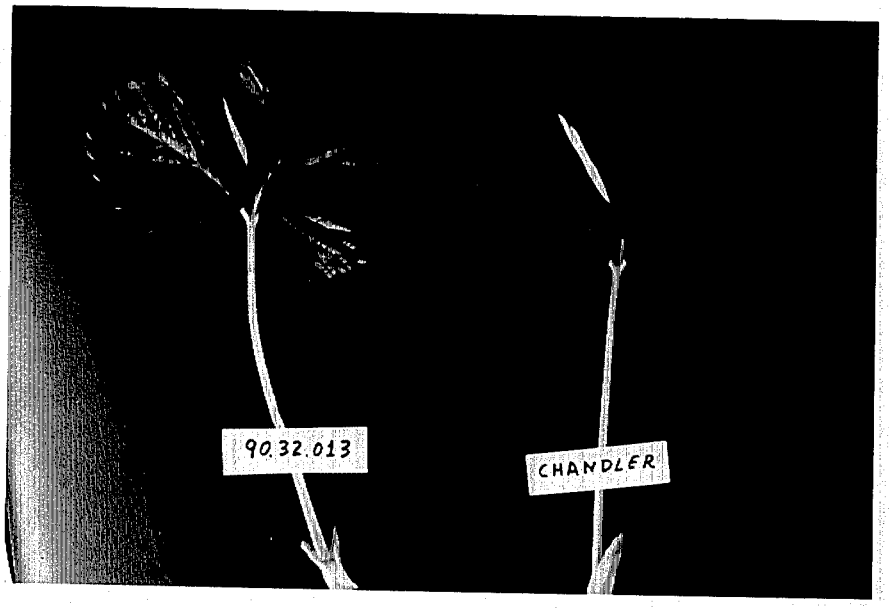
FIG. 8 shows a comparison of the foliage of the new variety (designated 90.32.013) and of the variety 'Chander'.
Figure 9:
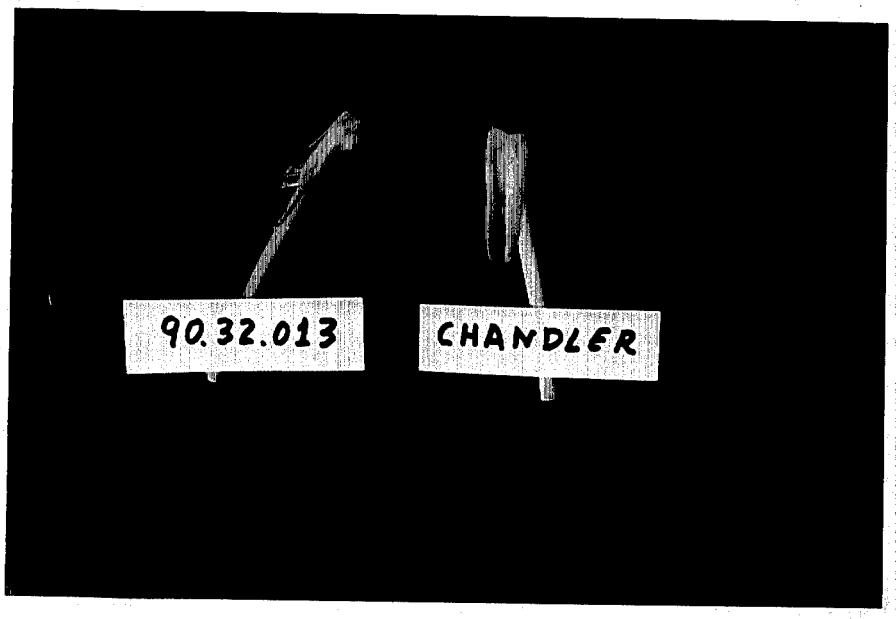
Figure 10:
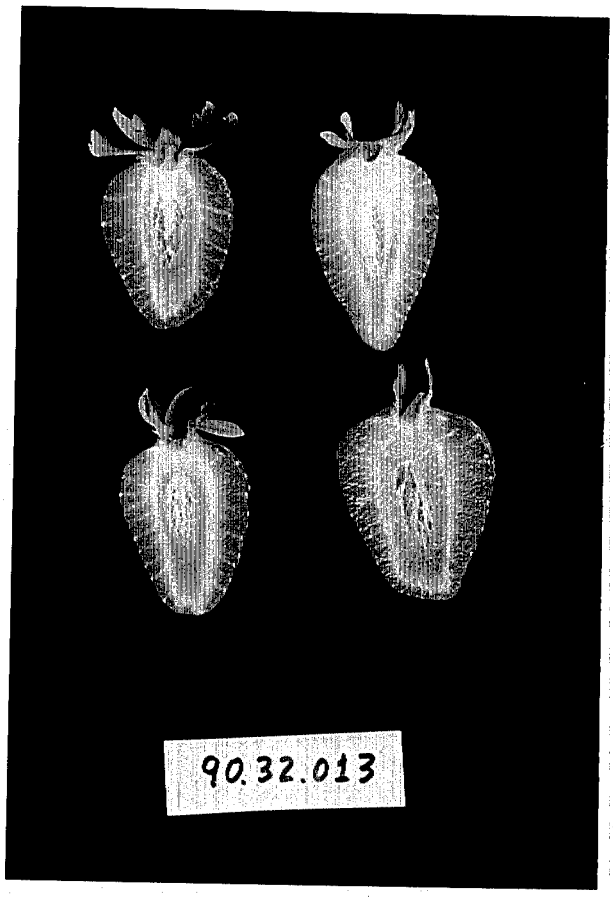
Figure 11:
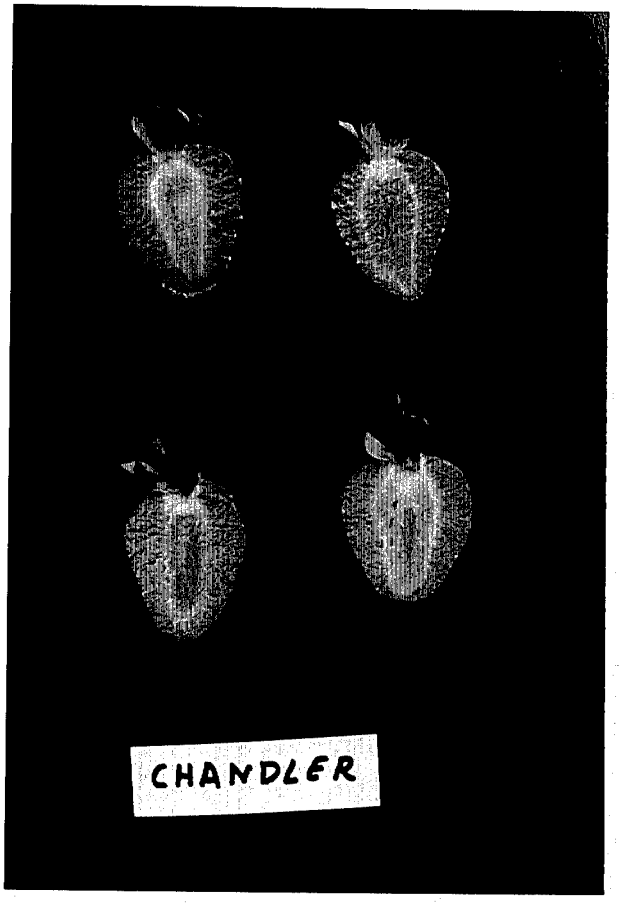
Figure 12:
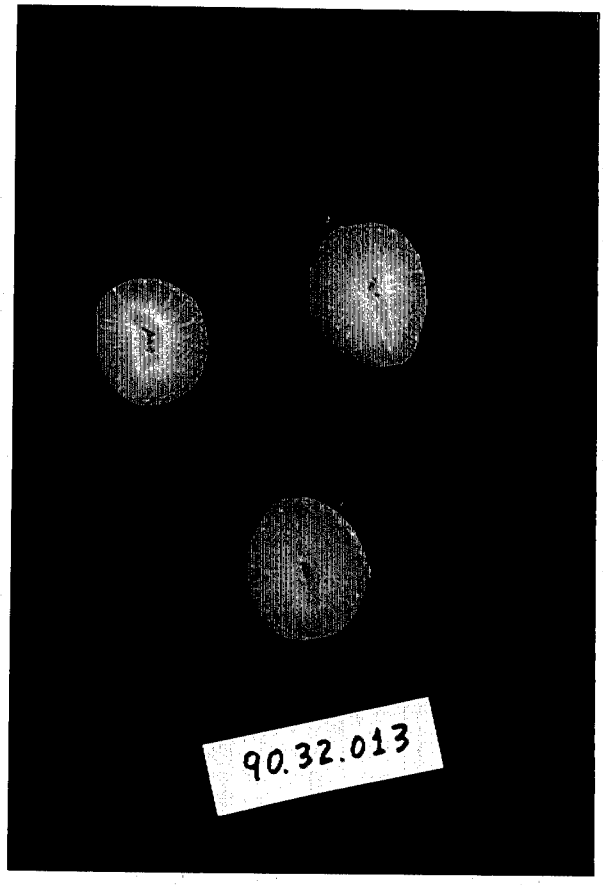
Figure 13:
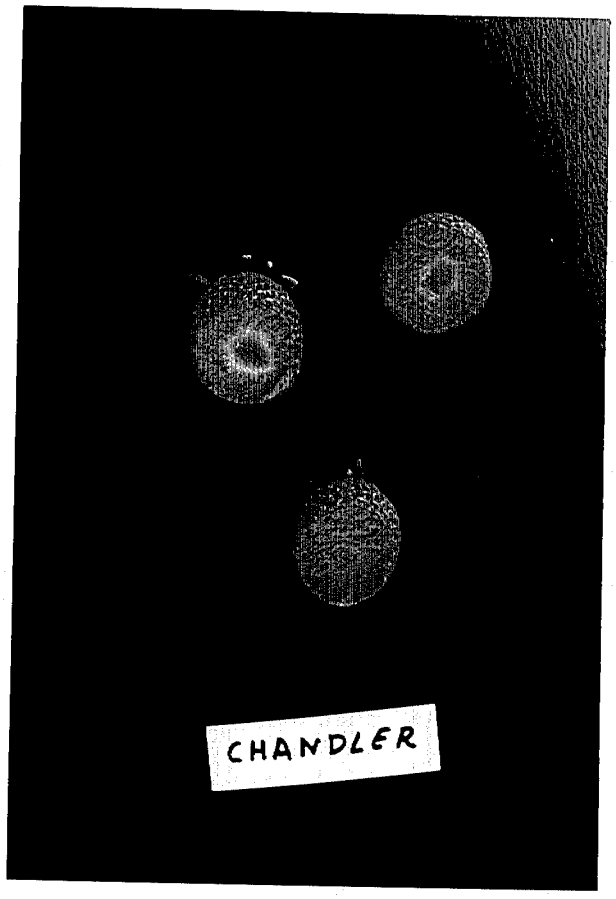

FIG. 9 shows a comparison of the stipules shape and color of the new variety (designated 90.32.013) and of 'Chandler'; and FIGS. 10, 11, 12 and 13 are photographs of the cross-section of fruit of the new variety (designated 90.32.013, FIGS. 10 and 12) and of 'Chandler' (FIGS. 11 and 13).

DESCRIPTION OF THE NEW VARIETY

The following detailed descriptin of the new variety is based upon observations taken of plants and fruit grown "underglass", i.e. undertunnel, in the farm of La Mogalla in Cartaya (Huelva), Spain, 7°W., 37°N., 45 feet elevation.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

Propagation: The new variety is principally propagated by way of runners. Although propagation by runners is presently preferred, other known methods of propagating strawberry plants may be used. Strawberries root well after transplanting.

General: 'Arena' is a short day variety that needs an induction to flowering by chilling, such as occurs at a high elevation nursery (fresh plant) or with cold storage (referred to as a frigo).

Production: Plants described are from high elevation nursery: include two repetitions with 100 plants per repetition.

*Date of planting.*—20th Oct. 1994 in Cartaya (Huelva).

Comparison with 'Chandler': The new variety is compared with 'Chandler' in FIGS. 8, 9, 10, 11, 12, and 13. As can be seen, the flesh color in 'Chandler' is relatively even whereas in the fruit of 'Arena' it is slightly uneven.

| | Accumulated production of 1st quality fruit (g/plant) | | | | | | | |
|---|---|---|---|---|---|---|---|---|
| Variety | 28-Fb | 31-MR | 30-Ap | 31-My | 1st–2nd | To-tal | % 2nd | Size G/fruit |
| Milsei | 101 | 287 | 538 | 732 | 732 + 97 | 829 | 11.5 | 22–22 |
| Cartuno | 84 | 269 | 478 | 652 | 652 + 66 | 718 | 9.0 | 22–21 |
| Cartdos | 81 | 225 | 420 | 535 | 535 + 92 | 627 | 15.0 | 19–19 |
| Cartcua | 85 | 193 | 376 | 550 | 550 + 116 | 666 | 17.5 | 22–22 |
| Arena | 100 | 256 | 450 | 661 | 661 + 81 | 742 | 11.0 | 22–21 |
| Oso Grande | 80 | 232 | 462 | 636 | 636 + 84 | 720 | 11.5 | 22–22 |

| | FRUIT ANALYSIS | | | | |
|---|---|---|---|---|---|
| | MIL-SEI | ARE-NA | OSO GRANDE | CAR-TUNO | CART-CUA |
| Firmness (KG) | 0.7 | 0.6 | 0.8 | 0.7 | 0.7 |
| Humidity & Volatile Matter (%) | 92.89 | 93.06 | 93.49 | 91.97 | 93.28 |
| Dry Matter (%) | 7.11 | 6.94 | 6.51 | 8.03 | 6.72 |
| PH | 3.37 | 3.55 | 3.54 | 3.74 | 3.62 |
| Acidity as Anhydride Citric (%) | 0.87 | 0.81 | 0.72 | 0.55 | 0.83 |
| Soluble Solids (°Brix) | 5.4 | 6.2 | 5.7 | 7.5 | 6.5 |
| Maturity Index | 6.21 | 7.65 | 7.92 | 13.63 | 7.83 |
| Content in Ascorbic Acid (ppm) | 421 | 427 | 427 | 450 | 380 |
| Tonality: Dominant (nm.) | 450 | 460 | 460 | 470 | 450 |
| Luminosity (%) (Transmittance to 460 nm) | 43.7 | 36.5 | 39.1 | 43.7 | 49.1 |

The following additional information is provided to further describe the new variety.

Variety: Arena.

Classification: Fragaria, L.

Plant:
- *Habit.*—Flat globose.
- *Density.*—Medium.
- *Vigour.*—Medium.
- *Height.*—About 18 cm.
- *Width.*—About 23 cm.

Leaf: Dark on upper side.
- *Length.*—About 13 cm.
- *Width.*—About 10.5 cm.
- *Cross section.*—Slightly concave.
- *Blistering.*—Strong.
- *Number of leaflets.*—Three.

Terminal leaflet:
- *Length/width ratio.*—Longer than broad.
- *Length.*—About 7.3 cm.
- *Width.*—About 7 cm.
- *Shape of base.*—Obtuse.
- *Shape of teeth.*—Obtuse.

Petiole:
- *Position of hairs.*—Outwards.
- *Length.*—About 13 cm.

Stipule:
- *Anthocyanin coloration.*—Medium.

Stolons:
- *Number.*—Medium.

Anthocyanin coloration: Medium.
- *Thickness.*—Medium.
- *Pubescence.*—Medium.

Inflorescence:
- *Position relative to foliage.*—Beneath.

Flower:
- *Size.*—Large.
- *Size of calyx relative to corolla.*—Larger.
- *Size of inner calyx relative to outer.*—Larger.
- *Spacing of petals.*—Overlapping.

Petal:
- *Length/width ratio.*—Broader than long.

Fruiting truss:
- *Attitude.*—Semi-erect.

Fruit:
- *Ratio of length/maximum width.*—Longer than broad.

Primary fruit:
- *Length.*—About 5.8 cm.
- *Width.*—About 4.1 cm.

Secondary fruit:
- *Length.*—About 4.5 cm.
- *Width.*—About 3.2 cm.
- *Size.*—Large.
- *Predominant shape.*—Conical/almost cylindrical.
- *Difference in shapes between primary and secondary fruits.*—Moderate.

Fruit:
- *Band without achenes.*—Narrow.
- *Color of achenes.*—Amber red.
- *Unevenness of surface.*—Weak.
- *Color.*—Red.
- *Evenness of color.*—Even.
- *Glossiness.*—Strong.
- *Insertion of achenes.*—Below surface.
- *Insertion of calyx.*—Level.
- *Position of the calyx segment.*—Reflexed.
- *Size of calyx in relation to fruit diameter.*—Same size.
- *Adherence of calyx.*—Strong.
- *Firmness.*—Firm.
- *Color of flesh.*—Medium red.

*Evenness of color of the flesh.*—Slightly uneven.
*Sweetness.*—Medium.
*Acidity.*—Medium.
*Time of flowering.*—Early.
*Time of ripening.*—Early.
*Type of bearing.*—Not remontant.
*Chilling.*—Weak.
*Planting date.*—27 Oct. 1993.
10% *Flowering.*—9 Dec. 1993.
*First mature fruits.*—25 Jan. 1994.
*Maturity* (15–20 gms/plant).—8 Feb. 1994.

Note: The growing period in Huelva, Spain, where the observations were made, is between about January 25 and May 31 of each year, with a maximum production at about mid-April.

Disease resistance: No particular sensitivity to any disease or parasite has been observed for 'Arena.'

What is claimed is:

1. A new and distinct variety of strawberry plant, substantially as shown and described.

* * * * *

UNITED STATES PATENT AND TRADEMARK OFFICE

CERTIFICATE OF CORRECTION

PATENT NO. : Plant 9,770
DATED : December 31, 1996
INVENTOR(S) : Jose M. A. Lopez It is certified that error appears in the above-indentified patent and that said Letters Patent is hereby corrected as shown below:

Column 1, line 36, change "Chandler" to -- 'Chandler' --.
Column 1, line 47, change "'Chander'" to -- 'Chandler' --.
Column 2, line 6, change "consical" to -- conical --.
Column 2, line 16, change "ILLUSTRATION" to -- ILLUSTRATIONS --.
Column 2, line 19, replace "designated s" with -- designated as --.
Column 2, line 24, change "fleshcoloration" to -- flesh coloration --.
Column 2, line 34, change "leave" to -- leaf --.
Column 2, line 36, change "'Chander' to -- 'Chandler' --.
Column 2, line 46, change "descriptin" to -- discription --.

Signed and Sealed this

Tenth Day of February, 1998

*Attest:*

Bruce Lehman

BRUCE LEHMAN

*Attesting Officer*

*Commissioner of Patents and Trademarks*